United States Patent [19]
Tsukada et al.

[11] Patent Number: 5,250,168
[45] Date of Patent: Oct. 5, 1993

[54] INTEGRATED ION SENSOR

[75] Inventors: Keiji Tsukada, Kastuta; Yuji Miyahara, Hitachi; Yasuhisa Shibata, Ibaraki; Yoshio Watanabe, Hitachi, all of Japan

[73] Assignee: Hitachi, Ltd., Tokyo, Japan

[21] Appl. No.: 723,952

[22] Filed: Jul. 1, 1991

[30] Foreign Application Priority Data
Jul. 3, 1990 [JP] Japan .................. 2-175738

[51] Int. Cl.⁵ .............................. G01N 27/26
[52] U.S. Cl. ..................... 204/416; 204/419; 204/422; 204/435; 204/415
[58] Field of Search ............ 204/415, 416, 419, 422, 204/435, 403, 414

[56] References Cited

U.S. PATENT DOCUMENTS 4,020,830  5/1977  Johnson et al. ............ 204/415
4,691,167  9/1987  Vlekkert et al. ............ 204/416
4,909,921  3/1990  Ito ............................. 204/403

OTHER PUBLICATIONS

"ISFET's Using Inorganic Gate Thin Films", IEEE Transactions on Electron Devices, vol. ED-26 No. 12, 1979, pp. 1939–1944.
"The Extended Gate Chemically Sensitive Field Effect Transistor as Multi-Species Microprobe", Sensors & Actuators, 4, 1983, pp. 291–298.

Primary Examiner—John Niebling
Assistant Examiner—Bruce F. Bell
Attorney, Agent, or Firm—Fay, Sharpe, Beall, Fagan, Minnich & McKee

[57] ABSTRACT

Disclosed is an integrated ion sensor, which comprises at least one ion selective membrane sensitive to ions contained in a solution to be measured for detecting the concentration of the ions, a signal processing circuit for inputting a detected signal obtained by the ion selective membrane through a conductive member and fetching the detected signal through MOSFETs or the like included in an input stage to process the same, a reference electrode disposed in the measuring environment made by the solution to be measured and to be set to a predetermined voltage relationship between the reference electrode and the ion selective membrane, and a power supply having negative and positive terminals for supplying a driving power to the signal processing circuit through the terminals, one of the terminals being connected to the reference electrode, wherein the signal processing circuit is set to an active state at a voltage set to the reference electrode by controlling the threshold value of at least one of the MOSFETs of the signal processing circuit.

28 Claims, 5 Drawing Sheets

INTEGRATED ION SENSOR

BACKGROUND OF THE INVENTION

1. Field of the Invention

The present invention relates to an integrated ion sensor, and more specifically, to an integrated ion sensor for measuring an electrolytic component and the like in a solution such as blood, urine, water in a river, and the like.

2. Description of the Related Art

An ion sensitive FET (ISFET) as an ion sensor making use of a MOSFET is generally arranged such that an ion selective membrane is directly formed on a gate insulation film without forming a gate electrode. A measuring circuit making use of an ISFET having this arrangement is, for example, described in IEEE Transactions on Electron Devices, vol. ED-26, No. 12 (1979), pp 1939–1944. The measuring circuit described in this literature needs a power supply for making a voltage and current between the drain and source of the ISFET constant, respectively and a power supply for imposing a proper voltage on a reference electrode provided for the purpose of making a sensor circuit active to process a signal.

Since the measuring circuit using the ISFET arranged as described above needs the two power supplies for the sensor circuit and the reference electrode, the number of wirings is increased and thus a device is made large and complex. Further, when the ion sensor is composed of a plurality of sensors each having a different ion selective membrane and simultaneously measures a plurality of different kinds of ions in a solution by using the sensors, although one reference electrode is commonly used for the sensors, the ion sensor needs measuring sensor circuits that are as many as the sensors, which makes the arrangement of the ion sensor more complex. In particular, when the above ion sensor is arranged such that the sensor circuits and reference electrode are assembled in a catheter and the ion sensor is miniaturized to measure in vivo in an organism, a disadvantage arises in that the number of lead wires to be connected to an external power supply and measuring circuit is increased.

While a preferred embodiment has been set forth with specific details, further embodiments, modifications and variations are contemplated according to the broader aspects of the present invention, all as determined by the spirit and scope of the following claims. Sensors and Actuators, 4, (1983), pp 291–298 discloses the arrangement of another ISFET, which transmits a signal regarding an ion concentration detected by the ion selective membrane to the gate electrode of a MOSFET through a signal line, as shown in FIG. 2 of the literature.

When the ion sensor having the ion selective membrane electrically connected to the gate electrode of the MOSFET through the signal line composed of, for example, polysilicon, as described above, is used for a long time, water molecules and the like in a solution to be measured pass through the ion selective membrane and enters the signal line and gate electrode to oxide or dissolve them. Accordingly, the state of the interface between the ion selective membrane and the signal line or gate electrode is made unstable, and thus a disadvantage arises in that the change in the responsive characteristics of the ion sensor caused by an elapse of time is increased.

Conventionally known is a voltage follower circuit serving as an electric circuit arrangement having a gain set to 1. When the voltage follower circuit has two MOSFETs provided at the input stage thereof, an ion sensor including an ISFET and generating an output with a gain of 1 can be made by replacing one of the MOSFETs with the ISFET. To actually realize a voltage follower circuit generating the above output, the structural characteristics, i.e., the thickness of the oxide film of a gate, channel length, channel width and the like of a MOSFET to be disposed on an input stage must strictly coincide with those of an ISFET to be disposed thereon. Since, however, the ISFET having the ion selective membrane electrically connected to the gate electrode through the signal line has the great change in the responsive characteristics caused by an elapse of time, as described above, when the ion sensor is composed of the voltage follower circuit, the characteristics of the ISFET does not coincide with those of the MOSFET when the ion sensor is used for a long time. As a result, since the gain of the circuit is offset from 1 and thus the output from the ion sensor must be corrected, the circuit arrangement is made complex due to the provision of a corrective circuit.

OBJECT AND SUMMARY OF THE INVENTION

A first object of the present invention is to provide an integrated ion sensor provided with a reference electrode, the integrated ion sensor being operated by a single power supply, having a simplified circuit arrangement and wiring, and arranged compactly.

A second object of the present invention is to provide an integrated ion sensor having measuring characteristics which are little changed by an elapse of time even if the ion sensor is used for a long time and carrying out a stable and accurate measuring operation.

A first integrated ion sensor according to the present invention comprises at least one ion selective membrane sensitive to ions contained in an solution to be measured for detecting the concentration of the ions, a signal processing circuit for inputting a detected signal obtained by the ion selective membrane through a conductive member and fetching the detected signal through MOSFETs or the like included in an input stage to process the same, a reference electrode disposed in the measuring environment made by the solution to be measured and to be set to predetermined voltage relationship between the reference electrode and the ion selective membrane, and a power supply having two negative and positive terminals for supplying a driving power to the signal processing circuit through the any terminals and any one of the terminals being connected to the reference electrode, wherein the signal processing circuit is set to an active state at a voltage set to the voltage of the reference electrode by controlling the threshold value of at least one of the MOSFETs of the signal processing circuit.

An integrated ion sensor according to the present invention may be arranged such that the ion selective membrane and the signal processing circuit in the above first arrangement are formed as a single semiconductor integrated circuit device and the reference electrode is formed as a separate member.

An integrated ion sensor according to the present invention may be arranged such that the electric circuit unit composed of the ion selective membrane and the signal processing circuit and the reference electrode in the first arrangement are accommodated in a catheter. In this arrangement, further, the ion selective membrane, signal processing circuit, and reference electrode may be formed as a semiconductor integrated circuit device.

In the above respective arrangements, when the ion sensor may be formed, for example, to a depletion type by controlling the threshold value of the MOSFETs or the like at the input stage, when, for example, they are made, the power supply to the sensor circuit also can be used as the power supply to the reference voltage, whereby the sensor circuit can be made compact as a whole and the number of lead wires can be reduced.

A second integrated ion sensor according to the present invention may be arranged such that the signal processing circuit in the above first arrangement is composed of a voltage follower circuit or a non-inverted amplifying circuit.

The integrated ion sensor according to the present invention may be arranged such that a metal film of any one of platinum group metal, gold, silver, and silver alloy or a metal oxide film of any one of palladium oxide, platinum oxide, and iridium oxide, which is connected to the gate electrode of the MOSFET and with which the ion selective membrane is covered, is used as the conductive member in the above first arrangement.

The integrated ion sensor according to the present invention may be arranged such that a metal film of any one of platinum group metal, gold, silver, and silver alloy or a metal oxide film of any one of palladium oxide, platinum oxide, and iridium oxide, which is connected to the gate electrode of the MOSFET and with which the ion selective membrane is covered, is used as the conductive member in the above second arrangement.

As apparent from the above, the provision of the protection layer composed of the platinum layer or the like between the ion selective membrane and the gate electrode of the MOSFET prevents water molecules and the like entering through the ion selective membrane from adversely affecting the sensor circuit. When the ion sensor has a plurality of MOSFETs (or ISFET devices having an insulating gate structure) provided at the input stage thereof and is particularly arranged as the voltage follower circuit or the non-inverted amplifying circuit, the protection layer as the platinum layer or the like is interposed between the ion selective membrane and the gate electrode of the MOSFETs to thereby provide a necessary protection with the sensor circuit, similarly to the above.

DETAILED DESCRIPTION OF PREFERRED EMBODIMENTS

Embodiments of the present invention will be described below with reference to the attached drawings.

Figure 1:
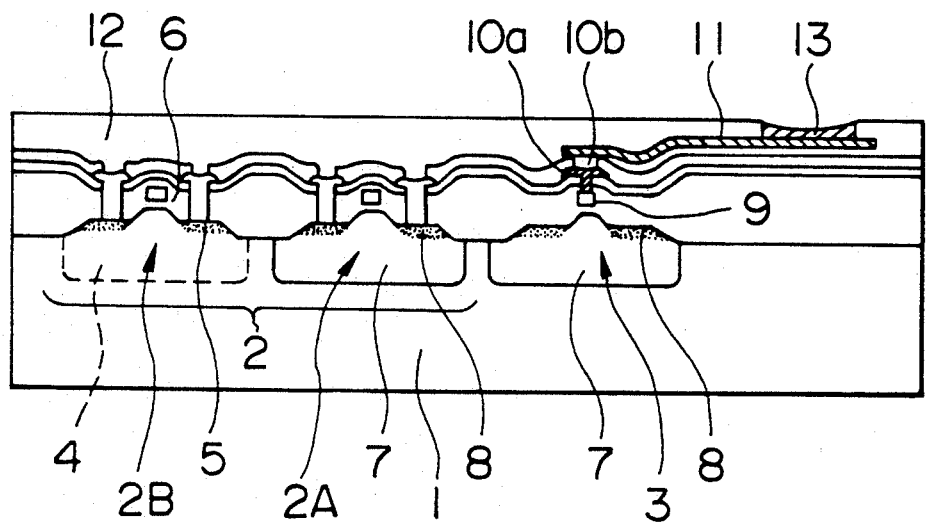
FIG. 1 is a cross sectional view of a main part of an integrated ion sensor according to the present invention.

FIG. 1 shows the cross section of a semiconductor device for various elements forming the sensor circuit of an integrated ion sensor according to the present invention. The sensor circuit is used to process a detected signal. In FIG. 1, 1 designates a silicon substrate on which a plurality of various semiconductor devices are formed; 2 designates a CMOS device composed of an nMOS FET (2A) and pMOS (2B); and 3 designates an ISFET device formed by providing an ion selective membrane with the gate electrode of a MOSFET through a conductive member, as described later. The above pMOS FET (2B) is separated from other semiconductor devices by an nWELL 4 formed to the silicon substrate 1. The source and drain of the pMOS FET (2B) are formed of a p+ diffused layer 5, respectively and SiO$_2$ is used for the gate insulation film 6 thereof. On the other hand, the nMOS FET (2A) and ISFET device 3 are separated from other semiconductor devices by a pWELL 7 formed to the silicon substrate 1, and an n+ diffused layer 8 is used for the source and drain thereof. The ISFET device 3 essentially has the same arrangement as that of the MOSFET devices. Further, an aluminium electrode 10a is formed on a gate electrode 9 composed of polysilicon and connected thereto, and a platinum layer 11 connected to the aluminium electrode 10a through a titanium layer 10b is disposed above the aluminium electrode 10a. The titanium layer 10b serves as an adhesive layer.

The upper surface of the ion sensor device is almost entirely covered with a polyimide film 12 and thus the upper surface of the device is entirely protected by the polyimide film 12. Further, a portion of the polyimide film 12 forms at least one groove of, for example, a circular shape and an ion selective membrane 13 is disposed therein. The above platinum layer 11 is extended to the circular opening where the ion selective membrane 13 is disposed in the state that the opening is surrounded with the polyimide film 12. The extreme end of the platinum layer 11 has substantially the same configuration as that of the ion selective membrane 13 and is covered with the ion selective membrane 13. With this arrangement, the platinum layer 11 is substantially electrically connected to the gate electrode 9 in the state that the extreme end thereof is covered with the ion selective membrane 13. The platinum layer 11 corresponds to the above conductive member disposed between the gate electrode 9 and the ion selective membrane 13.

Figure 2:
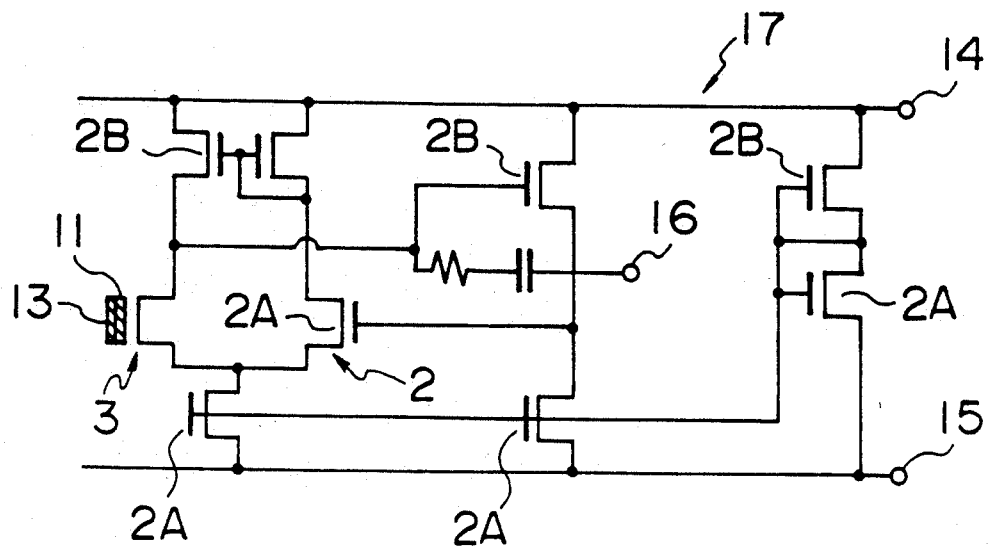
FIG. 2 is an electric circuit diagram of an integrated ion sensor.

FIG. 2 shows the sensor circuit as a whole formed in the sensor device having the above arrangement. As apparent from the electric circuit diagram, the sensor circuit 17 of the ion sensor is arranged as a voltage follower circuit using the CMOS device 2 and ISFET device 3. The voltage follower circuit has the two semiconductor devices of the nMOS (2A) and ISFET device 3 at the input stage thereof, wherein the ISFET device 3 is formed as a non-inverted input terminal and the nMOS (2A) is formed as an inverted input terminal. In the voltage follower circuit shown in FIG. 2, a DC power supply such as a battery or the like is connected between terminals 14 and 15 and a measured output voltage is derived from an output terminal 16. The terminal 14 is a power supply terminal and the terminal 15 is a ground terminal. The sensor circuit having the above arrangement has a function to process a detected signal output from the ion selective membrane 13.

Figure 3:
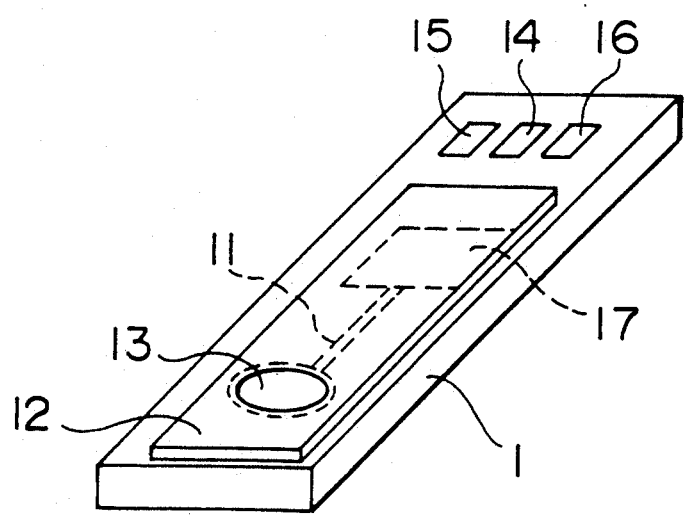
FIG. 3 is an outer perspective view of an integrated ion sensor.

FIG. 3 is a perspective view showing the outside appearance of the above sensor device of the ion sensor. The voltage follower circuit shown in FIG. 2 is formed in the interior of the device as an arrangement including the CMOS device 2 and ISFET device 3 and denoted at 17, and the upper surface of the voltage follower circuit is covered with the polyimide film 12 to protect the sensor circuit 17 from a solution to be measured. As described above, the groove composed of a circular opening is defined to the predetermined position of the polyimide film 12 and the ion selective membrane 13 is disposed therein. As described with reference to FIG. 1, the ISFET device is provided with the platinum layer 11 connected to the gate electrode of the MOSFET on which the ISFET device is based and the platinum layer 11 is extended to the position on this side in FIG. 3 where the ion selective membrane 13 is disposed. The configuration of the extreme end of the platinum layer 11 is substantially the same as that of the ion selective membrane 13, which covers the extreme end of the platinum layer 11. With this arrangement, the gate electrode of the ISFET device 3 is electrically connected to the ion selective membrane 13 through the platinum layer 11. Also, the above power supply terminal 14, ground terminal 15, and output terminal 16 are disposed in a line on the silicon substrate 1 at the end thereof opposite to the end where the ion selective membrane 13 is disposed.

The integrated ion sensor having the above arrangement is provided with the platinum layer 11 having the function to protect the sensor circuit 17, which is interposed between the gate electrode 9 of the ISFET device and the ion selective membrane 13, and the platinum layer 11 covered by the ion selective membrane 13 is electrically connected to the gate electrode 9. The platinum layer 11 prevents the possibility that alkali ions and water molecules enter the interior of the sensor circuit through the ion selective membrane 13 when the device is dipped in a solution to be measured for a long time, so that the platinum layer 11 can protect a gate insulation film and the like. Accordingly, the platinum layer 11 can prevent the deterioration of the gate electrode, gate insulation film and the like below the ion selective membrane 13.

Further, since the sensor circuit is arranged as the voltage follower circuit and the platinum layer 11 covering the polymer-supported ion selective membrane 13 is electrically connected to the gate electrode of the ISFET device 3 serving as the non-inverted input terminal of the voltage follower circuit, the change of a potential in the ion selective membrane 13 corresponding to a target ion concentration in a solution to be measured can be directly output as it is. Further, since a sensor output is made to have a low impedance because the sensor circuit is arranged as the voltage follower circuit, noise can be lowered and thus an external measurement circuit having a simple arrangement can be used. Note that a non-inverted amplifying circuit may be used in place of the above voltage follower circuit, wherein a detected signal output from the ion selective membrane 13 is amplified by the non-inverted amplifying circuit and then subjected to a signal processing.

In the above embodiment, another metal film or metal oxide film may be used as the conductive member in place of the platinum layer 11 as long as they have characteristics similar to those of the platinum layer 11. The other metal film includes, for example, platinum group metal, gold, silver, and silver alloy and the metal oxide film includes palladium oxide (PdO), platinum oxide ($PtO_2$) and iridium oxide ($IrO_2$).

In the above embodiment, to enable the ion sensor to be used to the measurement requiring high accuracy in such a case as clinical examinations and the like, for example, a polymer-supported ion selective membrane having an ion selective material dispersed in a polymer together with a plasticizing agent must be used as the ion selective membrane in place of an inorganic material.

Next, how the integrated ion sensor having the above arrangement is used will be described with reference to FIG. 4.

Figure 4:
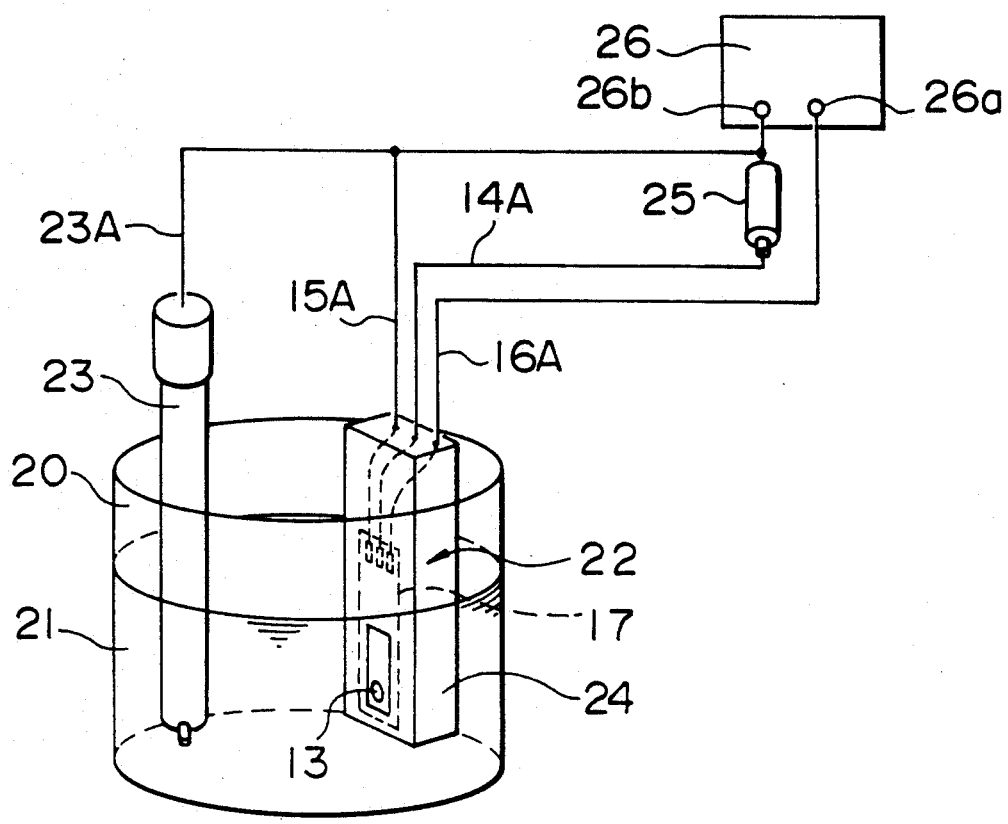
FIG. 4 is a diagram showing the measuring state and wiring state of an integrated ion sensor according to the present invention.

In FIG. 4, 20 designates a vessel and 21 designates a solution to be measured which is accommodated in the vessel 20. The ion concentration of the measuring solution 21 is measured by using the ion sensor according to the present invention. The sensor device 22 incorporating the sensor circuit 17 is placed in the measuring solution 21 in a substantially upright state so that the portion of the ion selective membrane 13 is dipped in the measuring solution 21 and the reference electrode 23 spaced apart from the sensor device 22 by a necessary distance is also placed in the solution. In operation, the sensor device 22 having the arrangement shown in FIG. 3 is actually encapsulated in a package 24 so that the entire portion thereof is covered therewith except only the ion selective membrane 13 which is exposed. Three lead wires 14A, 15A and 16A are derived from the upper surface of the package of the sensor device 22: the lead wire 14A derived from the power supply terminal 14 of the above voltage follower circuit is connected to the positive terminal of a battery 25; the lead wire 15A derived from the ground terminal 15 of the voltage follower circuit is connected to the negative terminal of the battery 25; and the lead wire 16A derived from the output terminal 16 of the voltage follower circuit is connected to one input terminal 26a of a voltmeter 26. The voltmeter 26 is supplied with an output signal from the sensor device 22 and displays the output signal as a voltage data. The lead wire 23A from the power supply terminal of the reference electrode 23 is connected to the negative terminal of the battery 25 and the negative terminal of the battery 25 is connected to the other input terminal 26b of the voltmeter 26.

The ion sensor cannot carry out a measuring operation only by the sensor device 22 including the sensor circuit 17 for effecting a signal processing and thus carries out the measuring operation in combination with the reference electrode 23. More specifically, the sensor circuit 17 cannot be set to an active state until a predetermined voltage relationship is established between the sensor circuit 17 reference electrode 23 and the.

The ion sensor arranged as described above can be operated as the ion sensor only by connecting the reference electrode 23 to the negative terminal of the battery 25 for supplying an electric power to the sensor device 22 and thus an exclusive power supply for the reference electrode 23 is not needed. Further, the reason why the sensor circuit can be operated only by connecting the reference electrode 23 to the negative terminal of the battery 25 and the sensor circuit as described above is that any one or both of the threshold values of the above nMOS (2A) and ISFET device 3 provided with the input stage of the voltage follower circuit can be controlled in the fabricating process of the sensor device 22 to be set to a proper value, which will be generally described with reference to FIG. 5.

Figure 5:
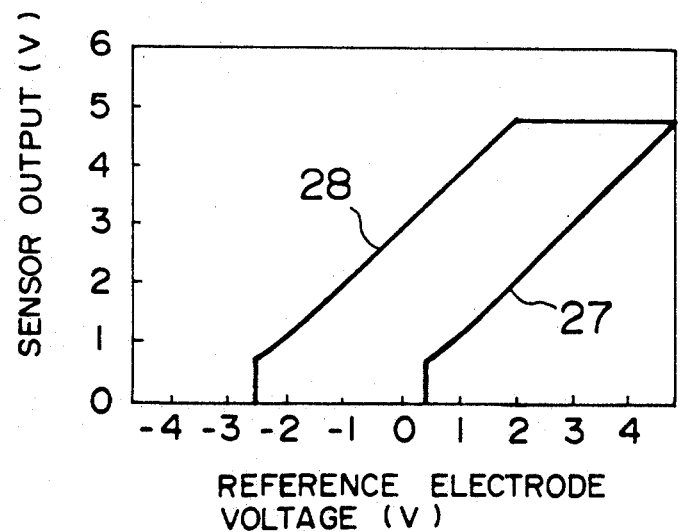
FIG. 5 is a characteristic diagram showing the relationship between a reference electrode voltage and a sensor output.

FIG. 5 shows the static characteristics of the output from the integrated ion sensor, wherein 27 shows the change of the output voltage from the sensor with respect to the voltage of the reference electrode when the threshold value of the sensor device 22 is not controlled. In this case, a power supply voltage to the sensor circuit is 5 volt and a buffer solution containing tris-boric acid of pH 7.0 is used as a measuring solution. As apparent from the static characteristics 27, when a zero volt is imposed on the reference electrode, the sensor produces no output. Accordingly, the ion sensor could not be used unless a voltage imposed on the reference electrode was set to an intermediate value relative to the value of the power supply voltage to the sensor circuit by the provision of an exclusive power supply to the reference electrode. Conversely, when, for example, the threshold value of the ISFET device is controlled in the process of fabricating the sensor device 22, as described above, to thereby arrange the ISFET device as a depletion type, a characteristic curve can be shifted to a negative side as shown by 28 in FIG. 5. With the shifted characteristic curve 28, even if a zero volt, i.e., a ground potential is imposed on the reference electrode, the ion sensor can perform the function thereof. More specifically, in the integrated ion sensor according to the present invention, the exclusive power supply is not needed to the reference electrode 23 and the sensor circuit 17 can be operated by setting the reference electrode 23 to the zero volt value by connecting it to the negative terminal of the battery 25 for the sensor device 22, whereby the arrangement of the ion sensor can be simplified. In particular, the number of the lead wires between the battery 25 as the power supply and the sensor device 22 including the sensor circuit 17 and the reference electrode 23 can be reduced, which is very advantageous when measurement is in vivo. Note that the simple change of the threshold value in the control enables the sensor circuit 17 to be operated by connecting the reference electrode 23 to the negative terminal of the battery 25.

As described above, according to the integrated ion sensor of the present invention, since the threshold value of at least the ISFET device at the input stage thereof can be controlled when the device is fabricated, the voltage relationship between the reference electrode and the sensor circuit is adjusted so that the power supply for the sensor circuit can be also used by the reference electrode, whereby the number of the power supplies is reduced, the circuit arrangement is simplified, and the number of the lead wires is reduced. Further, the provision of the platinum layer and the like between the gate electrode and ion selective membrane can stabilize the measurement effected by the ion sensor for a long time.

Figure 6:
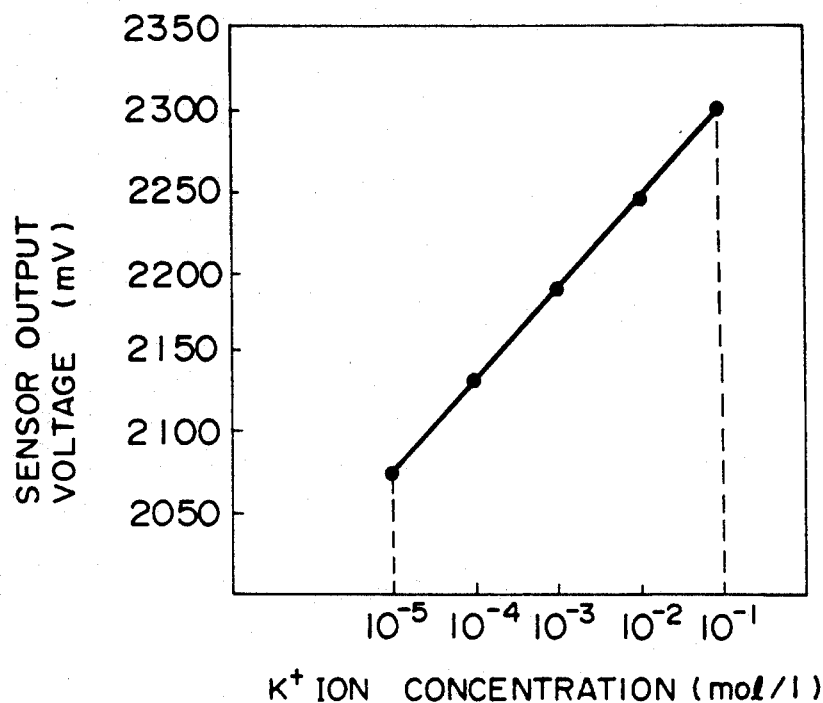
FIGS. 6 and 7 are diagrams showing examples of the result of measurement of an integrated ion sensor according to the present invention, respectively.
Figure 7:
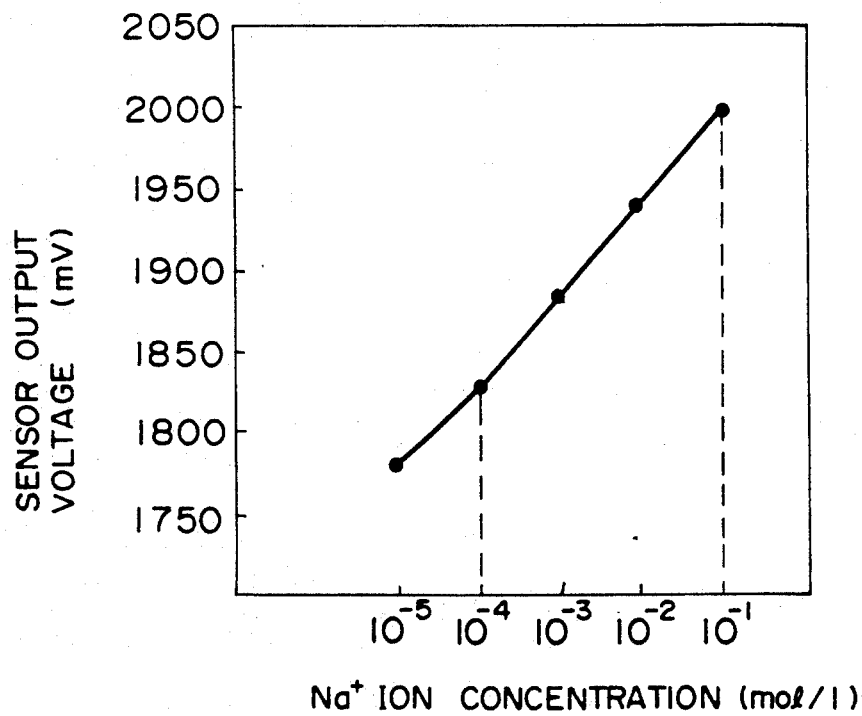

FIGS. 6 and 7 show the result of the measurement carried out by the integrated ion sensor according to the present invention. FIG. 6 is the response characteristics of a $K^+$ sensor using a $K^+$ ion selective membrane. As the $K^+$ ion selective membrane, variomycin was used for ligand, TOTM [Tri-(2-ethlhexyl)trimellitate] was used for a plasticizer member, and PVC (polyvinyl chloride) was used for a polymer matrix. As apparent from the result of the measurement, a linear response could be obtained in the range of from $10^{-1}$ to $10^{-5}$ mol/l and a sensitivity of 59.4 mV/decade was obtained by the sensor. FIG. 7 shows the response characteristics of a $Na^+$ sensor using a $Na^+$ ion selective membrane. As the $Na^+$ ion selective membrane, bis[(12-crown-4)methyl]methyldodecyl-malonate was used for ligand, TOTM was used for a plasticizer member, and PVC was used for a polymer matrix. As apparent from the result of the measurement, although the linear range of the $Na^+$ sensor was a little narrower than that of the $K^+$ sensor, a linear response was obtained in the range of from $10^{-1}$ to $10^{-4}$ mol/l and a sensitivity of 56.5 mV/decade was obtained by the sensor.

A second embodiment of the integrated ion sensor according to the present invention will be described with reference to FIGS. 8 and 9. The same numerals as used in the components in the above embodiment are used to designate substantially the same components.

Figure 8:
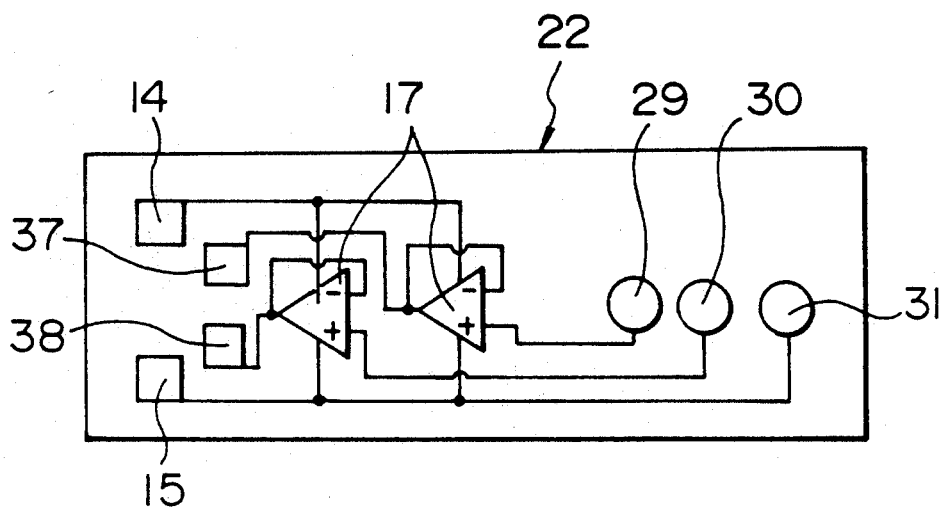
FIG. 8 is an electric circuit diagram showing another embodiment of an integrated ion sensor according to the present invention.
Figure 9:
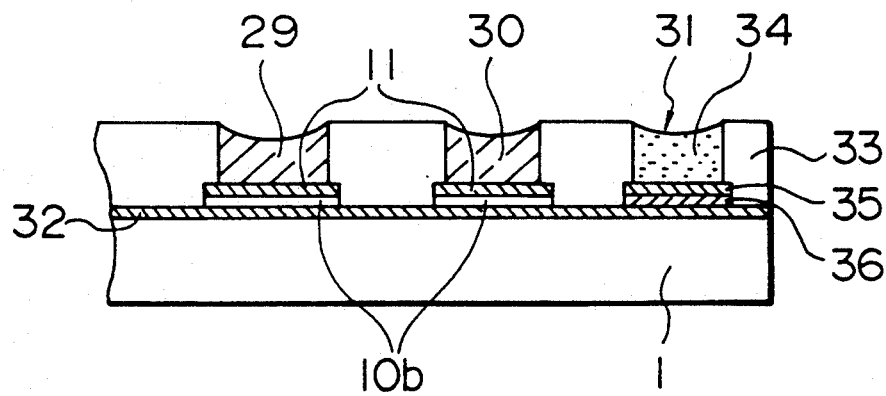
FIG. 9 is a cross sectional view showing the cross sectional structure of the ion selective unit of the integrated ion sensor of the above another embodiment.

In FIG. 8, a Na ion selective membrane 29, K ion selective membrane 30 and reference electrode 31 are provided at the extreme end of a sensor device 22. Accordingly, in this embodiment, two kinds of the ion selective membranes 29, 30 and the reference electrode 31 are formed on the single sensor device 22. As shown in FIG. 9, the various ion selective membranes 29, 30 and reference electrode 31 are separately formed on the oxide film 32 formed on a silicon substrate 1. A polyimide film 33 having holes, with which the various ion selective membranes and the gel for the reference electrode are filled, patterned thereto is used for the separation. Each of the ion selective membranes 29, 30 is composed of a mixed member of ligand and plasticizer member using polyvinyl chloride as a polymer matrix. Further, the Na ion selective membrane 29 and K ion selective membrane 30 are covered with a platinum layer 11 at their under surface, respectively. Since each of the platinum layers 11 is directly adhered to the silicon oxide film 32 with difficulty, titanium layers 10b are provided as an adhesive layer.

On the other hand, the reference electrode 31 is composed of a silver electrode 36 having a silver chloride 35 formed thereon, and electrolytic gel 34 mixed with potassium chloride, which covers the silver chloride 35.

Since the two ion selective membranes 29, 30 are disposed on the single device 22, two exclusive sensor circuits 17 are disposed in the device 22. In FIG. 8, output terminals 37,38 correspond to the sensor circuits 17 for the ion selective membranes 29 and 30, respectively. Further, since the reference electrode 31 is integrally assembled in the device 22, the reference electrode 31 is directly connected to the ground terminal 15 on the sensor device 22 which is connected to the negative terminal of a battery 25. Note that the ground terminal 15 serves as a ground terminal of the buffer amplifier of each sensor circuit 17.

The change of potentials of the ion selective membranes, which have arisen in the ion selective unit when it comes in contact with a solution to be measured, are transmitted to the ISFET devices of the non-inverted input terminal in the sensor circuits 17 corresponding to each ion selective membrane. Each of the sensor circuits 17 is energized by an external power supply through the respective lead wires connected to the power supply terminal 14 and ground terminal 15 of the sensor device 22. An output signal, i.e., sensor detection signal from each of the sensor circuits 17 is transmitted to an external measurement circuit through lead wires connected to respective output terminals 37, 38 to thereby calculate the concentrations of Na ions and K ions in a solution to be measured.

The Na ion sensor of the above embodiment could obtain 58.2 mV/decade and the K ion sensor thereof could obtain 59.3 mV/decade, similarly to the ion sensor of the first embodiment, and thus a sensitivity substantially near to a theoretical value could be obtained. Further, a problem of crosstalk did not arise between the sensors.

In the above second embodiment, when the number of the ISFET devices is generally set to n, the number of lead wires to be derived to the outside is n+2. In addition, when a conventional insulating gate type ISFET is used, lead wires for the drain and source of each ISFET are needed, and thus the sensor device 22 needs 2n lead wires for each ISFET and a single lead wire for the reference electrode. Accordingly, the integrated sensor device according to the present invention can greatly reduce the number of the lead wires.

Although, in the above embodiments, the object to be measured is an electrolytic component in a solution, dissolved components such as ammonia gas and the like can be measured by forming hydrophobic porous membranes to hold various inner solution layers on the upper portion of the ion selective unit or a biochemical component such as glucose can be measured by forming an immobilized enzyme membrane in place of the ion selective membrane, in a similar way.

We claim:

1. An integrated ion sensor, comprising:
   at least one ion selective membrane sensitive to ions contained in a solution to be measured for detecting the concentration of said ions to produce a corresponding detected signal;
   a signal processing circuit having field effect semiconductor devices, and for inputting the detected signal obtained by said ion selective membrane through said field effect semiconductor devices to process the same;
   a reference electrode disposed in a measuring environment made by the solution to be measured and set to a predetermined voltage relationship between said reference electrode and said ion selective membrane;
   a single power supply having a negative terminal and a positive terminal, said terminals being connected to said signal processing circuit for supplying a driving power to said signal processing circuit through said terminals, and one of said terminals being connected to said reference electrode, to provide the predetermined voltage relationship;
   said signal processing circuit including means to set an active state of the ion sensor at a voltage relative to the voltage of said reference electrode by controlling the threshold value of at least one of said field effect semiconductor devices.

2. An integrated ion sensor according to claim 1, wherein said ion selective membrane and said signal processing circuit are formed as a single semiconductor integrated circuit device, and said reference electrode is formed as a separate member.

3. An integrated ion sensor according to claim 1, including a catheter; and
   wherein an electric circuit unit composed of said ion selective membrane, said signal processing circuit and said reference electrode are accommodated in said catheter.

4. An integrated ion sensor according to claim 3, wherein said ion selective membrane, said signal processing circuit and said reference electrode are formed as a single semiconductor integrated circuit device.

5. An integrated ion sensor according to claim 1, wherein said signal processing circuit is composed of a voltage follower circuit.

6. An integrated ion sensor according to claim 1, wherein said signal processing circuit is composed of a non-inverted amplifying circuit.

7. An integrated ion sensor according to claim 1, further including an electrically conductive metal film of at least one or more of platinum group metal, gold, silver, and silver alloy electrically connected between the gate electrode of one of said field effect semiconductor devices and said ion selective membrane.

8. An integrated ion sensor according to claim 1, further including an electrically conductive metal oxide film of any one of palladium oxide, platinum oxide, and iridium oxide, electrically connected between the gate electrode of one of said field effect semiconductor devices and said ion selective membrane.

9. An integrated ion sensor according to claim 5, further including an electrically conductive metal film of at least one or more of platinum group metal, gold, silver, and silver alloy electrically connected between the gate electrode of one of said field effect semiconductor devices and said ion selective membrane.

10. An integrated ion sensor according to claim 6, further including an electrically conductive metal oxide film of any one of palladium oxide, platinum oxide, and iridium oxide, electrically connected between the gate electrode of one of said field effect semiconductor devices and said ion selective membrane.

11. An integrated ion sensor according to claim 1, wherein said signal processing circuit has an external low impedance output and said signal processing circuit is a voltage follower circuit for low noise output.

12. An integrated ion sensor according to claim 1, further including a surface protecting layer having an opening in which said ion selective membrane is mounted, entirely covering a portion of a surface of said signal processing circuit, and being means for protecting the signal processing circuit, except for the portion of a surface, from said solution to be measured; and
   a conductive member positioned between said ion selective membrane and said portion of a surface of said signal processing circuit, said conductive member electrically connecting said ion selective membrane and a gate electrode of at least one of said field effect semiconductor devices, and said conductive member being means for protecting said at least one field effect semiconductor device from water molecules of the solution to be measured entering through said ion selective membrane to stabilize measurement effected by the ion sensor.

13. An integrated ion sensor according to claim 1, wherein at least one of said field effect semiconductor devices has a gate electrode directly connected to said ion selective membrane; and wherein said means to set provides said at least one of said field effect semiconductor devices as a depletion type with a characteristic curve shifted to a negative value relative to the voltage of the reference electrode.

14. An integrated ion sensor according to claim 1, further having external terminals consisting of said negative terminal, said positive terminal, and at least one output terminal of said signal processing circuit.

15. An integrated ion sensor according to claim 1, further having external terminals consisting of said negative terminal, said positive terminal, at least one output terminal of said signal processing circuit, and said reference electrode.

16. An integrated ion sensor according to claim 1, wherein there are a number n of said signal processing circuits and of said ion selective membranes respectively having output terminals, for measuring concentration of different ions; and further including
n+2 external terminals only, consisting of said n output terminals, said negative terminal and said positive terminal.

17. An integrated ion sensor according to claim 1, further including an electrically conductive member for protecting said field effect semiconductor devices from water molecules of said solution to be measured entering through said ion selective membrane.

18. An integrated ion sensor according to claim 17, wherein said conductive member is a metal film, and said ion selective membrane is disposed on said metal film in contact with and to partially cover a surface area of said metal film; and
wherein a gate electrode of one of said field effect semiconductor devices is electrically directly connected to said metal film.

19. An integrated ion sensor according to claim 17, wherein said conductive member is a metal film of any one of platinum group metal, gold, silver, silver alloy, palladium oxide, platinum oxide, and iridium oxide.

20. An integrated ion sensor according to claim 18, wherein said metal film is made of any one of platinum group metal, gold, silver, silver alloy, palladium oxide, platinum oxide, and iridium oxide.

21. An integrated ion sensor, comprising:
at least one ion selective membrane sensitive to ions contained in a solution to be measured for detecting the concentration of the ions and producing a corresponding detected signal;
a signal processing circuit for inputting the detected signal obtained by said ion selective membrane, and having at least one field effect semiconductor device included in an input stage to fetch the detected signal;
a surface protecting layer having an opening in which said ion selective membrane is mounted, entirely covering a portion of a surface of said signal processing circuit, and being means for protecting the signal processing circuit, except for the portion of a surface, from said solution to be measured; and
a conductive member positioned between said ion selective membrane and said portion of a surface of said signal processing circuit, said conducting member electrically connecting said ion selective membrane and a gate electrode of said at least one field effect semiconductor device, and said conductive member being means for protecting said at least one field effect semiconductor device from water molecules of the solution to be measured entering through said ion selective membrane to stabilize measurement effected by the ion sensor.

22. An integrated ion sensor according to claim 21, wherein said conductive member is made of at least one or more of platinum group metal, gold, silver, silver alloy, palladium oxide, platinum oxide, and iridium oxide.

23. An integrated ion sensor according to claim 21, wherein a portion of said conductive member completely seals the opening between said ion selective membrane and said signal processing circuit, and contacts said surface protecting layer surrounding the opening thereby to provide said means for protecting.

24. An integrated ion sensor according to claim 23, wherein said conductive member is made of at least one or more of platinum group metal, gold, silver, silver alloy, palladium oxide, platinum oxide, and iridium oxide.

25. An integrated ion sensor according to claim 21, wherein said conductive member is a metal film, said ion selective membrane is disposed in contact on said metal film, and said gate electrode is directly electrically connected to said metal film.

26. An integrated ion sensor according to claim 25, wherein said conductive member is made of at least one or more of platinum group metal, gold, silver, silver alloy, palladium oxide, platinum oxide, and iridium oxide.

27. An integrated ion sensor according to claim 21, wherein said means for protecting prevents hydration of an insulation film of the gate electrode.

28. An integrated ion sensor according to claim 21, wherein said means for protecting includes both the conductive member and the surface protecting layer completely protecting the signal processing circuit from contact with any water in the solution and thereby protecting an insulating film of the gate electrode from hydration.

* * * * *